United States Patent [19]

Page

[11] Patent Number: 5,056,540
[45] Date of Patent: Oct. 15, 1991

[54] TOOTH FLOSSER

[76] Inventor: Daniel A. Page, 2906 N. Main St., Crossville, Tenn. 38555

[21] Appl. No.: 509,600

[22] Filed: Apr. 16, 1990

[51] Int. Cl.⁵ ............................................ A61C 15/00
[52] U.S. Cl. ................................................... 132/323
[58] Field of Search ............... 132/323, 327, 324, 325, 132/326

[56] References Cited

U.S. PATENT DOCUMENTS

| | | | |
|---|---|---|---|
| 2,354,454 | 7/1944 | Geffner | 132/323 |
| 3,631,869 | 1/1972 | Espinosa | 132/323 |
| 3,892,249 | 7/1975 | Jones et al. | 132/323 |
| 4,192,330 | 3/1980 | Johnson | 132/323 |

FOREIGN PATENT DOCUMENTS

| | | | |
|---|---|---|---|
| 2508598 | 9/1975 | Fed. Rep. of Germany | 132/323 |
| 2222089 | 2/1990 | United Kingdom | 132/323 |

Primary Examiner—Cary E. O'Connor
Attorney, Agent, or Firm—Pitts & Brittian

[57] ABSTRACT

A tooth flossing device for making the task of flossing teeth easier, neater, and more effective. A handle, designed for being gripped by a hand of a user, carries a removable, replaceable cartridge attached to one end. This cartridge contains a length of dental floss stretched between two pole pieces which are just far enough apart to pass a tooth between them. A user inserts the cartridge end of the flosser into his mouth, pressing the length of floss between two adjacent teeth, repeating the action until the spaces between all teeth have been cleaned. A used cartridge can be quickly and easily removed from the handle and replaced by a new one by pressing a detent and sliding the old cartridge from engagement with the handle. When the fresh cartridge is inserted, the detent automatically locks it into position.

6 Claims, 2 Drawing Sheets

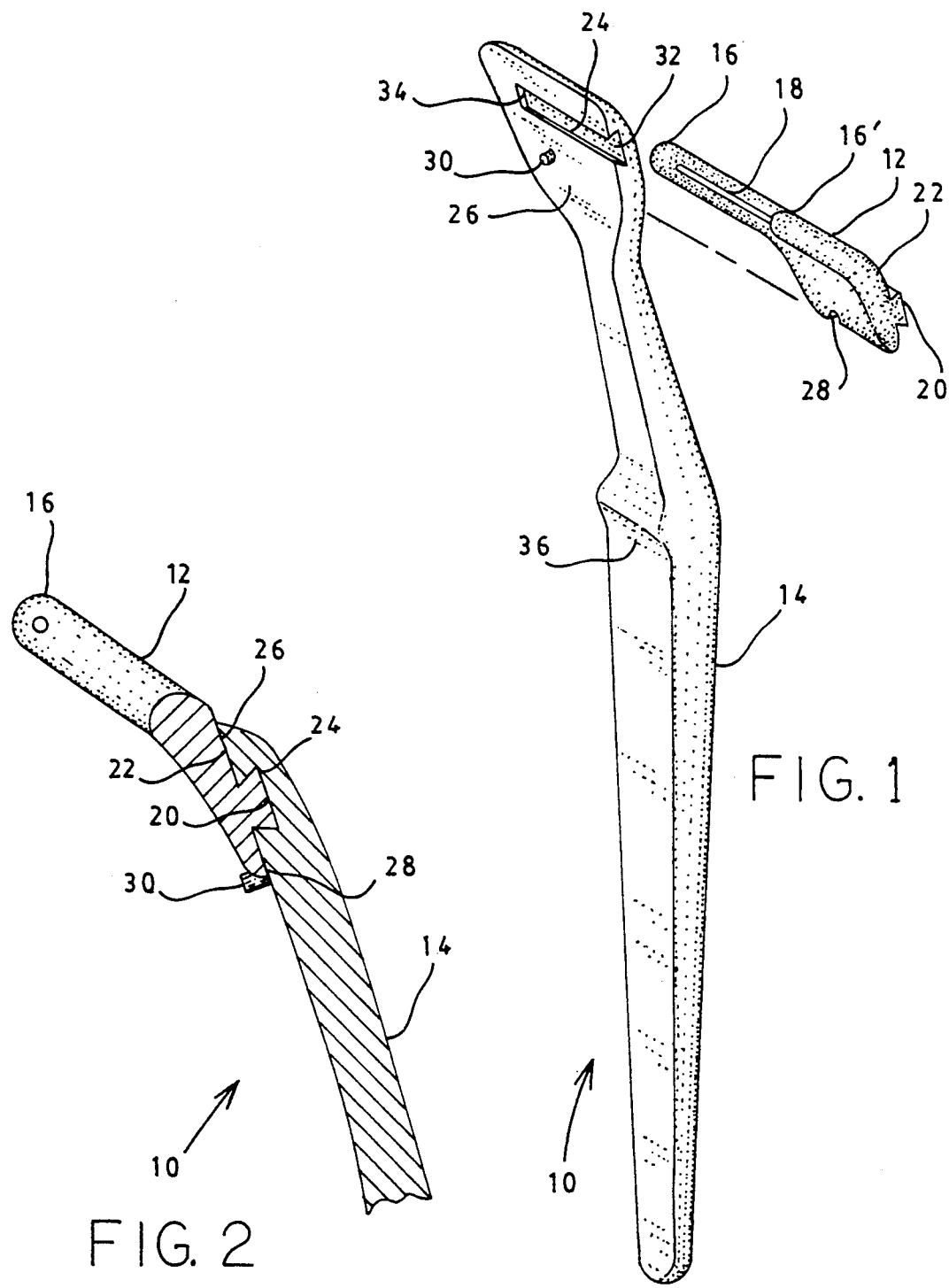

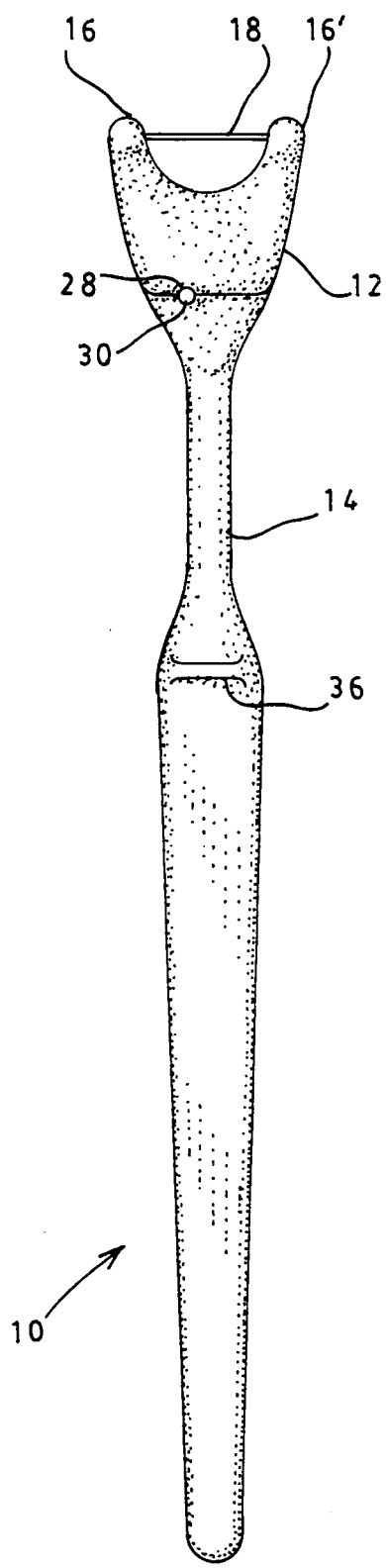
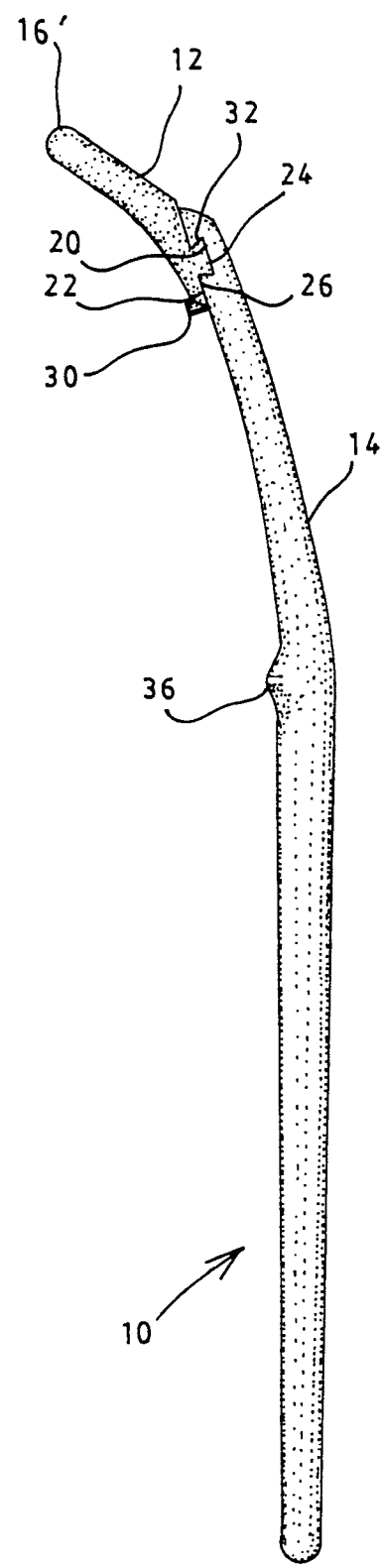
FIG. 3
FIG. 4

TOOTH FLOSSER

TECHNICAL FIELD

This device relates to dental care apparatuses in general, and more particularly concerns a tool for holding dental floss to more effectively and sanitarily perform the act of cleaning between the teeth.

BACKGROUND ART

It is well-known that dentists recommend the practice of flossing between the teeth as an adjunct to brushing. Heretofore, the act of flossing has necessitated making a good guess as to the length of floss needed, cutting such a length from the main package, wrapping a portion around a finger on each hand, inserting fingers and floss into the mouth, and pressing the floss between the teeth. Seldom, if ever, could one length of floss suffice to do more than four or five teeth before replacement was needed, together with drying of the mouth and hands.

The present invention eliminates the mess, the guesswork, and the difficulty of flossing the old-fashioned way. Not only is a single cartridge expected to be useful in flossing more teeth than previous methods, but with a supply of replaceable cartridges available, flossing becomes even easier and less messy than brushing.

BRIEF DESCRIPTION OF THE DRAWINGS

FIG. 1 is a perspective view of a device constructed in accordance with various features of the present invention, with a cartridge in detached juxtaposition thereto.

FIG. 2 is a detail view, partially in section, of a portion of the device of FIG. 1 showing the cartridge inserted into the handle.

FIG. 3 is a front elevation view of the device of FIG. 1.

FIG. 4 is a side elevation view of the device of FIG. 1.

DISCLOSURE OF THE INVENTION

A tooth flossing device for making the task of flossing teeth easier, neater, and more effective. A handle, designed for being gripped by a hand of a user, carries a removable, replaceable cartridge attached to one end. This cartridge contains a length of dental floss stretched between two pole pieces which are just far enough apart to allow a tooth to pass between them. A user inserts the cartridge end of the flosser into his mouth, pressing the length of floss between two adjacent teeth, repeating the action until the spaces between all teeth have been cleaned. A used cartridge can be quickly and easily removed from the handle and replaced by a new one by pressing a detent and sliding the old cartridge from engagement with the handle. When the fresh cartridge is inserted, the detent automatically locks it into position. A portion of the handle can be bent at a divergent angle for more efficient access to all of a user's teeth. A portion of the handle can also be formed into a wider and flatter space to aid in being gripped by a user's thumb.

BEST MODE FOR CARRYING OUT THE INVENTION

A device for flossing the teeth, constructed in accordance with various features of the present invention, is illustrated generally at 10 in the figures. In FIG. 1, the device 10 is shown in perspective with a removable cartridge 12 in detached juxtaposition to a handle 14.

In a preferred embodiment, cartridge 12 is constructed of plastic or similar material found to be appropriate for repeated use in the mouth. A selected length of dental floss 18 is carried under suitable tension between pole piece 16 and 16' portions of cartridge 12. Cartridge 12 has an engaging face portion 22 for engaging with handle 14. A portion of engaging face 22 is formed into a tenon 20 for engaging a complementary mortise 24 which has been cut into a cartridge receiving portion 26 of handle 14. When tenon 20 of cartridge 12 is inserted into an open end 32 of mortise 24, notch 28 receivably engages with detent 30 of handle 14 to prevent the accidental disengagement of cartridge 12 from handle 14.

Handle 14 is preferably constructed of the same material as cartridge 12. A length of approximately five inches is appropriate for handle 14. An upper portion of handle 14 is made to diverge from the straight line of the lower portion so as to carry cartridge 12 to the most optimum position for flossing the teeth. An upper end of the divergent portion of handle 14 is fitted with a cartridge receiving portion 26 from which a portion of the material has been excised to form a mortise 24. When cartridge 12 is to be attached to handle 14, an end of tenon 20 is inserted into the open end 32 of mortise 24 and pressed inward until the closed end 34 of mortise 24 is reached. At that time, detent 30 automatically engages with notch 28 of cartridge 12, thereby preventing cartridge 12 from being accidentally withdrawn from engagement with handle 14. When withdrawal of cartridge 12 from handle 14 is desired, such as for replacing a used cartridge with a fresh one, detent 30 can be pressed in an outward direction from notch 28, releasably allowing cartridge 12 to be withdrawn. A portion of handle 14 can be formed into a thumb grip 36 to aid the user in holding the flossing device 10 in an optimum position for flossing the teeth.

In use, a cartridge 12 is attached to handle 14 in the manner just described. Handle 14 is then manipulated so as to place cartridge 12 in the mouth of a user with end poles 16 and 16' on opposite sides of a selected tooth. Handle 14 is then pressed so as to insert floss 18 into the space between two adjacent teeth. Repeated applications of insertion, withdrawal, reinsertion, and/or rotation may be required to adequately clean the space between the teeth. This process is repeated until all the spaces between the teeth have been cleaned.

Thus, it will be seen that there has been provided a description of a hand-held tool for use in flossing the teeth. In a preferred embodiment, disposable cartridges, each one containing a length of dental floss, can be inexpensively molded from plastic or similar material such that the use and disposal of a plurality of cartridges can be accomplished without becoming a significant expense. The use of such a device, with its inexpensive cartridges, is preferred, not only because flossing of the teeth is thus more effective, but also because it is no longer necessary to insert the fingers, given their probable lack of sanitation, into the mouth, with the attendant annoyance of having saliva all over the mouth, fingers, and floss.

While a preferred embodiment of a device constructed in accordance with various features of the present invention has been described herein, no attempt has been made to limit the device to such description.

Rather, such description has been intended to embody all possible variations and alternate constructions falling within the spirit and scope of the invention as defined in the appended claims.

Accordingly, this invention is limited only by the claims appended hereto, and their equivalents, when taken in combination with the complete description contained herein.

I claim:

1. A tooth flossing device for making the task of flossing teeth easier, neater and more effective, comprising:

handle means for being held and gripped by a hand of a user, said handle means defining a cartridge receiving portion at an end thereof;

removable, replaceable dental floss-carrying cartridge means having two pole pieces for carrying between said pole pieces a selected length of dental floss in taut suspension to be removably and repeatedly inserted between a user's teeth; and interlocking means for releasably securing said cartridge means to said cartridge receiving portion of said handle means whereby said replaceable floss-carrying cartridge is rigidly carried by said handle means when mounted thereon, said interlocking means including a mortise and tenon dovetail joint.

2. The flossing device of claim 1 wherein a portion of said handle means is bent at a divergent angle for more efficient access to all of a user's teeth.

3. The flossing device of claim 1 wherein said handle means possesses a thumb detent space thereon for receiving a user's thumb.

4. The flossing device of claim 1 wherein said cartridge receiving means has a mortise half of the dovetail joint formed therein, and said replaceable cartridge carrying a tenon of said dovetail joint.

5. A hand-held tooth-flossing device for use in flossing the teeth of a user, comprising:

a handle for being held by the hand of a user to apply said tooth-flossing device in the act of flossing teeth, and for receiving and carrying a replaceable cartridge carrying a selected length of dental floss;

a replaceable cartridge carrying a selected length of dental floss and carried by said handle by means of an interlocking joint means;

an interlocking joint means for attaching said replaceable cartridge to said handle, said interlocking joint comprising a mortise and tenon dovetail joint, said mortise having an open end and a closed end; and detent means for automatically locking said floss-carrying replaceable cartridge in usable alignment with said handle when said tenon of said cartridge is inserted into said open end of said mortise and pressed to the limit of lateral travel allowed by said closed end of said mortise, and for allowing said cartridge to be released for disposal when said detent means is pressed in a releasing direction.

6. The flossing device of claim 5 wherein said handle and said cartridge cooperatively form an arc shape for optimum access to all of a user's teeth.

* * * * *